United States Patent [19]

Beck et al.

[11] 4,016,065
[45] Apr. 5, 1977

[54] ELECTROLYTIC FIELD RESPIROMETER

[75] Inventors: Sidney Marion Beck; Campbell Moore Gilmour, both of Moscow, Idaho

[73] Assignee: Idaho Research Foundation, Inc., Moscow, Idaho

[22] Filed: Oct. 16, 1975

[21] Appl. No.: 622,991

[52] U.S. Cl. .............................. 204/275; 204/1 T; 204/129; 204/195 R; 204/271; 204/278
[51] Int. Cl.[2] ..................... C25B 1/02; C25B 1/04
[58] Field of Search ............ 204/1 T, 129, 129 UX, 204/195 R, 195 T, 212, 230, 265, 271, 275, 277, 278, 266

[56] References Cited

UNITED STATES PATENTS

| | | | |
|---|---|---|---|
| 1,101,078 | 6/1914 | Kiefer | 204/129 X |
| 1,819,917 | 8/1931 | Niederreither et al. | 204/129 |
| 3,045,665 | 7/1962 | Moyat | 204/129 X |
| 3,616,436 | 10/1971 | Haas | 204/230 X |
| 3,661,753 | 5/1972 | Aylward et al. | 204/212 |
| 3,725,236 | 4/1973 | Johnson, Jr. | 204/195 R |

OTHER PUBLICATIONS

Hesse, "A Textbook of Soil Chemical Analysis", published by John Murray, Ltd., London, (1971), pp. 226–238.
McGarity et al., "Use of an Electrolytic Respirometer . . . Soil", Canadian Jrnl. of Microbiol., vol. 4, (1958), pp. 303–316.
Oceanography International Corp., "The E/BOD Respirometer System", a descriptive brochure, Nov. 1971.

Primary Examiner—John H. Mack
Assistant Examiner—A. C. Prescott
Attorney, Agent, or Firm—Wells, St. John & Roberts

[57] ABSTRACT

The disclosed electrolytic field respirometer consists of a sample vessel in which oxygen is utilized by a biological sample. Oxygen is provided on demand from an electrolytic cell which is turned on when the electrolyte level in a contact tube rises because of decreased pressure in the sample vessel due to oxygen consumption. A compensating vessel is operatively connected to the electrolytic cell to balance pressure fluctuations due to changes in the environmental pressure or temperature to which the respirometer is subjected.

9 Claims, 1 Drawing Figure

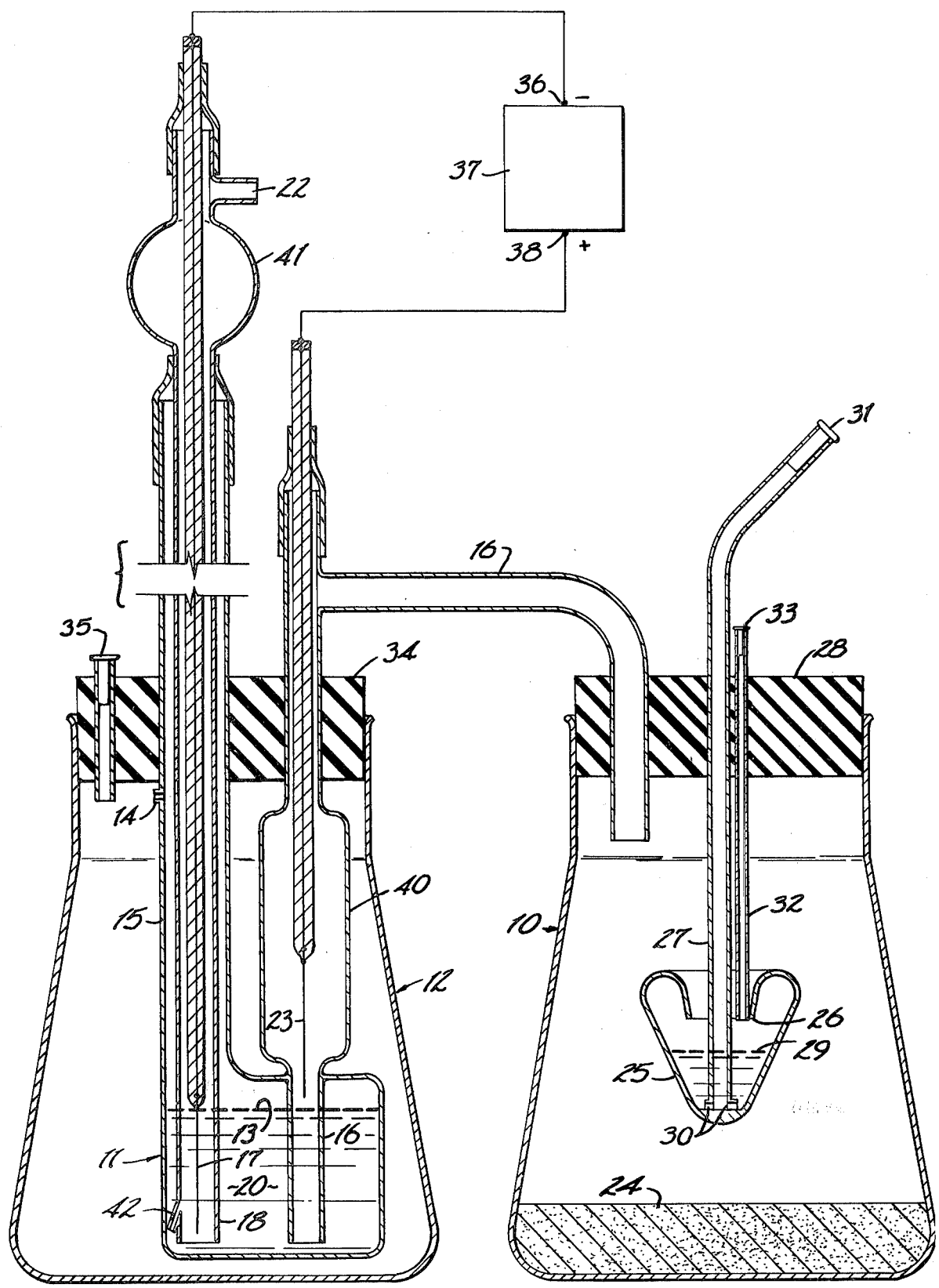

ELECTROLYTIC FIELD RESPIROMETER

BACKGROUND OF THE INVENTION studies

The electrolytic field respirometer is an apparatus for maintaining a constant oxygen atmosphere over a biological sample while measuring the carbon dioxide produced by the specimen. It allows the determination of carbon turnover values (carbon mineralization rates) in systems such as soils, decomposing forest litter, sewage sludge applied to land, and animal waste disposal systems. It may be used also to study respiration of microbial cultures, small animals, and tissue preparations. It is capable of indirectly measuring the rate of oxygen consumption in the above systems, as well as total oxygen consumption. In conjunction with a gas chromatograph, it is capable of being used for nitrogen fixation studies wherein the utilized or fixed nitrogen in a sample vessel is replaced by oxygen and results in an increased $O_2/N_2$ ratio in the sample vessel.

Early methods of measuring the rate of decomposition of organic matter relied upon periodic determination of the amount of carbon dioxide evolved by the sample. As an example, a definite area of soil might be covered with a container of known volume for a specific period of time. The carbon dioxide produced within the container during the test period would then be measured. In laboratory studies, the usual basic procedure was to keep a sample of soil in a vessel which also contained a vial of carbon dioxide absorbent. The carbon dioxide absorbed could be measured after a set period of time.

Incubation procedures are not fully satisfactory for the study of organic matter decomposition because the gradual depletion of oxygen during the test period affects microbial activity. One answer proposed to this problem was the use of barium peroxide to renew the diminishing oxygen supply during respiration. Other researchers supplied pure oxygen at atmospheric pressure, the oxygen being drawn into the sample vessel or flasks as carbon dioxide was absorbed. Another technique used in the part was to keep the soil in a vessel and draw over its surface a slow stream of carbon dioxide-free air. The air was then passed through a carbon dioxide absorbent and the carbon dioxide determined at known intervals of time.

In all of these prior methods, the necessary measurement of carbon dioxide evolution could be carried out only at definite intervals of time, not continuously, and none of these methods gave a complete picture of organic matter decomposition. It is desirable in this type of test to know the quantity and rate of oxygen uptake during decomposition. This information, plus periodic determination of carbon dioxide evolved, permits the calculation of the "respiratory quotient" $CO_2/O_2$, which gives an indication of the type of organic material decomposing.

More recent efforts have introduced the use of an electrolytic soil respirometer for measuring oxygen uptake, providing continuous replacement of oxygen by electrolysis as decomposition proceeds. In general, the sample is placed in a container with a sealed cover. A material is placed in the container to absorb carbon dioxide and a tube containing an electrode connects the sample container to a solution of electrolyte. Another electrode is immersed in the electrolyte. As carbon dioxide is absorbed by the sample, it creates a partial vacuum and the electrolyte is drawn up the tube until it makes contact with the electrode. Electrolysis of the water in the electrolyte results in delivery of oxygen to the container until the pressure is restored. At that time, the electrolyte sinks to its original level and electrolysis ceases. Hydrogen liberated during electrolysis can be measured at any time during or after cell operation.

Production of oxygen on demand by an electrolytic cell has been found unmanageable without external temperature controls, since the pressure fluctuations that result from temperature changes make the resulting reading unreliable. Prior electrolytic cell respirometers can be used only under laboratory conditions, where the sample container and electrolytic cell can be immersed in a controlled water bath or other incubator.

Laboratory use of the electrolytic respirometer in conjunction with testing of biological samples has demonstrated the versatility of this type of apparatus. The present apparatus was developed as a field unit, having internal temperature compensation and partial barometric compensation and eliminating the need for a water bath to control temperature. Basic requirements for the unit also were that it be small, simple, portable, versatile, and sufficiently inexpensive to be used in considerable numbers in field studies as well as in laboratory studies.

SUMMARY OF THE INVENTION

The electrolytic field respirometer disclosed in detail below basically comprises a sealed sample chamber or vessel that receives and holds an oxygen-consuming biological sample. Also located within the sample vessel is a suitable chemical for absorbing carbon dioxide produced by the sample. A second sealed compensating chamber or vessel is located physically proximate to the sample vessel so as to be subjected to the same general temperature and pressure changes as is the sample vessel. An electrolytic cell is provided within the confines of one of these vessels to maintain a constant oxygen atmosphere over the sample. The cell comprises a vessel containing electrolyte, an anode elevationally spaced upwardly adjacent to the electrolyte and a cathode immersed in the electrolyte. Each electrode is surrounded by an outlet tube and the two electrodes are operatively connected to a suitable source of direct current. The outlet tube surrounding the anode is in open communication with the interior of the sample vessel and provides for delivery of oxygen to the sample vessel on demand. The interior of the electrolyte cell vessel is vented, at an elevation above the electrolyte, in open communication with the interior of the compensating vessel. Thus, changes in the environmental temperature or pressure about the respective vessels will result in compensating pressure changes on the electrolyte and will cancel out one another with a minimum of disturbance of the monitored test results.

It is a first object of this invention to provide a practical design for an electrolytic respirometer capable of field use without supporting temperature controls, water baths or other external arrangements for monitoring or controlling temperature or pressure fluctuations in the system.

Another object of the invention is to provide a practical design for an electrolytic respirometer so that it can be maintained in the field over extended periods of time with a minimum of maintanance.

3

These and further objects will be evident from the following disclosure, taken together with the accompanying drawings.

DESCRIPTION OF THE DRAWING

An elevational cross sectional view through the center of a preferred embodiment of the invention.

PREFERRED EMBODIMENT OF THE INVENTION

The electrolytic field respirometer shown schematically in the drawing consists of a sample vessel 10 in which oxygen is utilized by a biological sample; an electrolytic cell 11 which is activated or turned on when the electrolyte level in a tube surrounding one electrode rises because of decreased pressure in the sample vessel due to oxygen consumption; and a compensating vessel 12 which minimizes the effect of temperature and barometric pressure fluctuations upon the electrolyte level 13 in the electrolytic cell 11. The apparatus is not totally sealed and must necessarily be open to the external atmosphere in order to permit escape of unwanted hydrogen generated by the electrolytic cell 11.

The embodiment illustrated by the drawing shows the use of two wide-mouth Erlenmeyer flasks for the sample vessel 10 and compensating vessel 12. Other containers or vessels, such as wide-mouth specimen jars with plastic screw caps, can be substituted. The sample vessel 10 and compensating vessel 12 might be formed as two separate chambers or compartments of a single vessel or other specially designed unit. During field use of the respirometer, the sample vessel 10 and compensating vessel 12 are located physically adjacent to one another so as to be generally subjected to identical fluctuations in environmental temperature and pressure.

The compensating vessel 12 as illustrated contains the electrolytic cell 11. It also encloses, as a confined gas space, the gaseous volume of vessel 12 external to the electrolytic cell 11. This confined gas provides part of the temperature and barometric compensation against fluctuations in the electrolyte level 13 of the electrolytic cell 11. It is in open communication with the interior of the electrolytic cell through a small aperture 14 in the outer support tube 15 that extends upwardly from the electrolytic cell 11. The lower end of the tube 15 is open to the electrolyte 20. The opposing compensation against electrolyte level fluctuation due to temperature or pressure changes is provided by the confined gas space within sample vessel 10 through a connecting tube 16.

The electrolytic cell 11 produces hydrogen at a platinum cathode 17 located within an open ended trap and escape tube 18 immersed in the electrolyte 20. The hydrogen is passed upward through tube 18 and exits at 22. Oxygen is produced at a platinum anode 23 and passes to the sample vessel 10 through connecting tube 16 as the sample within vessel 10 raises the electrolyte 20 from its level 13 until it contacts the tip of anode 23. This turns on the current within the cell 11 and results in generation of oxygen to replace that used by the sample as the water content of the electrolyte is subjected to electrolysis.

The sample 24 illustrated in the drawing is shown as a layer of soil. As oxygen is utilized by the sample 24, carbon dioxide is produced. This is absorbed by a chemical medium 29 located within a reservoir 25 suspended within the sealed interior of the sample vessel 10. The reservoir is shown as a cup having an inverted mushroom shape. The upper lip 26 of the reservoir 25 curves downward inside the cup to prevent splashing of liquid chemical materials from the reservoir 25 onto the sample 24 during movement of the apparatus.

The reservoir 25 is suspended within the vessel 10 by a tube 27, held in a fixed position by frictional engagement through the cap 28 that seals vessel 10. Tube 27 also allows removal of liquid material from within reservoir 25 through two small holes provided at opposite sides of the lower end of tube 27 within the interior of reservoir 25. One hole 30 is shown in the drawing, the other being diametrically opposed to it. Tube 27 is normally sealed by a plug 31 inserted in its upper end. A second tube 32 extends through cap 28 and is normally closed by a venting plug 33. Tube 32 is opened by release of plug 33 during removal of material from reservoir 25. The lower end of tube 32 extends into reservoir 25 to permit rinsing of the reservoir by passage of water through tube 32.

The compensating vessel 12 is also sealed, being provided with a cap 34 that supports the electrolytic cell 11 by means of tube 18 and outer support tube 15. A removable plug 35 permits venting of the compensating vessel 12 when needed.

The cathode 17 is electrically connected to the negative terminal 36 of a DC power supply 37. The anode 23 is similarly connected to the positive terminal 38 of power supply 37. Both connections are made through sealed ends of the respective tubes within which the electrodes are mounted. The power source 37 can be either a battery or other reliable direct current supply such as is typically available in a laboratory.

The electrolyte 20 can be any suitable conductive liquid which will generate hydrogen and oxygen when subjected to a direct current through electrodes in contact with the electrolyte. One example is sodium sulphate, which has been used successfully with the illustrated apparatus as 8.0% of the anhydrous salt in distilled water. Another suitable possibility is sulfuric acid. Other electrolytes can be used, so long as they do not generate undesirable levels of toxic ozone or other materials, rather than oxygen.

With the desired electrolyte of sodium sulphate, the power supply 37 may consist of two 12 volt storage batteries for operation of several units at one location in remote field experiments. When using a direct current power supply other than batteries, the system has been usually operated at about 20 – 25 volts DC when using one to four units, and up to 40 volts DC when using sixteen to twenty of the units. The multiple units have been used in parallel connection to the power supply.

The medium 29 within reservoir 25 for absorbing carbon dioxide can be any suitable chemical capable of absorbing the gas as it is evolved by sample 24. A suitable example is sodium hydroxide in a solution that is 2 to 5 Normal. Other chemical materials cana be substituted.

The electrolytic cell 11 decomposes the water of the electrolyte 20 to produce hydrogen, which escapes to the atmosphere through exit 22, and oxygen, which is delivered to sample 24 through connecting tube 16. The rate of biological activity of sample 24 determines the rate of electrolysis.

The rate of electrolysis may be monitored by measuring the rate of hydrogen evolved. This can be accomplished by use of a water-filled gas buret inverted in a water reservoir (not shown). The volume of hydrogen produced is measured by connecting the hydrogen exit 22 to the buret and measuring resulting water displacement. The rate of electrolysis can also be followed by using a constant current or coulometric power supply (now shown) having an integrating timer to record the total quantity of electricity used by the electrolytic cell 13.

Sampling for carbon dioxide measurement is accomplished by evacuating the alkali through tube 27 by use of a pump or double-valve rubber gas-collecting aspirator bulb (not shown). Thus, the unit fulfills the essential need for measurement of electrolytic cell activity as well as carbon dioxide production.

The tubes 16 and 18 are respectively formed with safety bulbs shown at 40 and 41. The volume of each bulb 40, 41 should be at least 10% larger than the volume of electrolyte 20 within the cell 11 so as to be fully capable of containing the electrolyte.

The electrolyte level within cell 11 is maintained by periodic addition of water through the hydrogen exit 22.

Anode 23 acts as the controlling switch for the electrolytic cell 11. To prevent cathode 17 from acting as a shut-off switch during periods of increasing barometric pressure, a small upward indentation 42 is provided adjacent the lower end of tube 18. An upwardly inclined opening is formed through indentation 42 for escape of air to the interior of cell 11. The cathode 17 extends below the level of the opening through indentation 42 and is thus kept always in contact with the electrolyte 20.

The electrodes 23, 17 must be located at a sufficiently high elevation within the respective tubes 16, 18 to prevent the generated gases from bubbling out from the bottom of the tubes and mixing with each other. The isolation tubes surrounding the respective electrodes are positioned vertically to discourage, by diffusion, the electrolytic formation of acidic and alkaline concentration gradients in the electrolyte 20 around the electrodes 17, 23 and possible formation of undesirable electrolytic gas products, such as ozone.

The sample vessel 10 and compensating vessel 12 may be constructed at any convenient size, but they should contain, as nearly as possible, the same gas volume acting through the appropriate openings and tubes on the surface of the electrolyte 20. The gas volumes may be equalized by variation of the size of sample 24 or by adding water, marbles or sealed plastic or glass spheres of appropriate size within either vessel.

The respirometer may be modified from the design shown in the drawing to provide mounting of the electrolytic cell 11 along with the alkali-containing reservoir 25 within the sample vessel 10. In this case, the outer support tube 15 is vented, at an elevation of the level of the electrolyte 20, to the interior of the sealed empty compensating vessel 12. This has the disadvantage of leaving the compensating vessel 12 empty, while the sample vessel 10 is very crowded. This arrangement unbalances the compensating gas volumes in the two vessels if they are constructed of identical size. It has the advantage, however, of permitting the electrolytically produced oxygen to be liberated directly into the atmosphere of the sample vessel 10 and does not require it to diffuse through any connecting tubes between the two vessels.

This respirometer is unique in that it is small enough, simple enough, and mobile enough to be used in field studies. It may be operated in remote areas where no power line is available by using two 12-volt storage batteries in series as the power source. It does not require a constant temperature bath, because it is self-compensating for temperature changes. It is compensated against increasing barometric pressure by generation of oxygen to cause a matching increase in gas pressure in the sample vessel. Large and sudden decreases in barometric pressure may cause electrolyte to rise in the hydrogen escape tube, but this is partially compensated for by oxygen consumption by the sample, and if the sample is large enough, causes no trouble.

Banks of 16 respirometers have performed satisfactorily with the pairs of flasks buried in the soil for periods of over thirty days, during which time the air temperature varied from 2° C to 30° C, and the top half inch of soil reached at least 52° C during certain days and 50° C during certain nights.

Extremely good laboratory quality data on carbon turnover rates were obtained in these field tests. It is possible to get good carbon turnover rate data and hald-life data on observations as short as one or two days.

The respirometer has many potential uses. Although it was designed as a field unit, it may also be used in the laboratory. It can be used in forest litter decomposition studies. Also, it is well-suited to the carrying out of carbon turnover studies in various environmental pollution problems. Much work needs to be done in the area of sanitary engineering with respect to sewage disposal on land, effects of trace metals on sludge and waste decomposition rates, and the fate of new industrial wastes when they are applied to land. This respirometer is ideally suited for field studies of these areas.

It is recognized that laboratory and field methodology do not always complement one another. Yet the need for field oriented data in the waste decomposition areas has become quite apparent, particularly from the viewpoint of variable stresses imposed by temperature-moisture fluctuations. It is our feeling that the field respirometer will provide comparative information for use in establishing realistic carbon turnover values and waste loading boundaries. Of some significance is the finding that out field and laboratory methods proved to be compatible.

Various modifications can be made in the specific design and geometry of the apparatus illustrated without deviating from the basic arrangement of the system. For this reason, the details described above are not intended to limit the scope of the invention, which is set out in the following claims.

Having thus described out invention, we claim:
1. In an electrolytic field respirometer:
    sealed sample chamber means for receiving an oxygen-consuming biological sample;
    means located within the sample chamber means for absorbing carbon dioxide;
    sealed compensating chamber means located physically proximate to said chamber means so as to be subjected to environmental temperature and pressure variations substantially identical to those to which the sample chamber means is subjected;
    electrolytic cell means for maintaining a constant oxygen atmosphere within the sample chamber means, said electroltyic cell means comprising:

a. an enclosed vessel containing a volume of electrolyte capable of releasing hydrogen and oxygen when subjected to electrolysis;
b. an anode located within the vessel at a position spaced upwardly adjacent to the normal level of electrolyte within the vessel;
c. a cathode located within the vessel at an elevational position such that it is immersed within the electrolyte;
d. first outlet means for delivery of oxygen from the vessel during operation of the electrolyte cell, said first outlet means being in open communication with the interior of the enclosed vessel and having an open lower end surrounding the anode;
e. second outlet means for delivery of hydrogen during operation of the electrolytic cell, said second outlet means being in open communication with the interior of the enclosed vessel and having an open lower end surrounding the cathode;
a direct current supply having positive and negative terminals respectively connected to the anode and cathode;
the first outlet means of the electrolytic cell being in open communication with the interior of the sample chamber means;
the interior of the enclosed vessel of the electrolytic cell being vented, at an elevation above the normal level of the electrolyte, in open communication with the interior of the compensating chamber means.

2. The apparatus set out in claim 1 wherein the second outlet means of the electrolytic cell is open to atmosphere.

3. The apparatus set out in claim 1 wherein said open lower end of the second outlet means terminates at an elevation below the normal level of the electrolyte within the enclosed vessel of the electrolytic cell.

4. The apparatus set out in claim 1 wherein the open lower end of the first outlet means is located at an elevation below the normal level of the electrolyte within the enclosed vessel of the electrolytic cell.

5. The apparatus set out in claim 1 wherein the respective open lower ends of the first and second outlet means are in the form of vertical tubes extending downwardly within the enclosed vessel of the electroltyic cell and are immersed in the electrolyte for isolation of gas evolved at the anode and cathode, respectively, during operation of the electrolytic cell.

6. The apparatus set out in claim 1 wherein the respective interior gas volume of the sample chamber means and the compensating chamber means in open communication with the interior of the enclosed vessel are substantially identical to one another.

7. The apparatus set out in claim 1 wherein the means for absorbing carbon dioxide is located within an upwardly open reservoir suspended within the sample chamber means, said reservoir having a downwardly projecting lip formed about its upper periphery for minimizing spillage during movement of the sample chamber means.

8. The apparatus set out in claim 3 wherein the second outlet means of the electrolytic cell is open to atmosphere.

9. The apparatus as set out by claim 8 wherein the cathode includes a lower end that is immersed in the electrolyte and wherein the second outlet means includes an inclined opening upwardly adjacent the lower cathode end with an upper opening end facing the cathode and a lower opening end facing away from the cathode.

* * * * *